United States Patent
Paul et al.

(10) Patent No.: US 10,143,544 B2
(45) Date of Patent: Dec. 4, 2018

(54) LOW PROFILE INTRALUMINAL MEDICAL DEVICES

(71) Applicant: Cook Medical Technologies LLC, Bloomington, IN (US)

(72) Inventors: Ram H. Paul, Bloomington, IN (US); Charles W. Agnew, West Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 408 days.

(21) Appl. No.: 14/839,239

(22) Filed: Aug. 28, 2015

(65) Prior Publication Data
US 2016/0058537 A1    Mar. 3, 2016

Related U.S. Application Data

(60) Provisional application No. 62/043,577, filed on Aug. 29, 2014.

(51) Int. Cl.
*A61F 2/01* (2006.01)

(52) U.S. Cl.
CPC .......... *A61F 2/01* (2013.01); *A61F 2002/016* (2013.01); *A61F 2230/0008* (2013.01); *A61F 2230/0076* (2013.01)

(58) Field of Classification Search
CPC .................. A61F 2/01; A61F 2002/016; A61F 2230/0076; A61F 2230/0008
See application file for complete search history.

(56) References Cited

U.S. PATENT DOCUMENTS

| | | | |
|---|---|---|---|
| 4,494,531 A | 1/1985 | Gianturco | |
| 4,832,055 A * | 5/1989 | Palestrant | A61F 2/01 128/899 |
| 4,994,077 A | 2/1991 | Dobben | |
| 5,324,304 A * | 6/1994 | Rasmussen | A61F 2/01 128/899 |
| 5,607,465 A | 3/1997 | Camilli | |
| 6,200,336 B1 | 3/2001 | Pavcnik et al. | |
| 6,391,045 B1 * | 5/2002 | Kim | A61F 2/01 128/899 |
| 6,623,506 B2 | 9/2003 | McGuckin, Jr. et al. | |

(Continued)

FOREIGN PATENT DOCUMENTS

| | | |
|---|---|---|
| WO | WO2009088957 | 7/2009 |
| WO | WO2010099209 | 9/2010 |

OTHER PUBLICATIONS

International Searching Authority, The International Search Report and Written Opinion of the International Searching Authority, May 20, 2010, for International Application No. PCT/US2010/025245.

(Continued)

*Primary Examiner* — Julie A Szpira
(74) *Attorney, Agent, or Firm* — Buchanan Van Tuinen LLC (57) ABSTRACT

A low profile intraluminal medical device includes first, second and third wire members that define arcuate paths having only a single sigmoidal curve. Connectors join the wire members. The medical device can be used by itself or as a component in a medical device that includes other components, such as a prosthetic valve, occluder, or filter.

20 Claims, 7 Drawing Sheets

(56) References Cited

U.S. PATENT DOCUMENTS

| | | | |
|---|---|---|---|
| 6,706,054 B2 * | 3/2004 | Wessman et al. | A61F 2/01 606/200 |
| 6,783,538 B2 * | 8/2004 | McGuckin, Jr. | A61F 2/01 606/200 |
| 7,128,759 B2 | 10/2006 | Osborne et al. | |
| 7,303,571 B2 | 12/2007 | Makower et al. | |
| 7,361,189 B2 | 4/2008 | Case et al. | |
| 7,569,071 B2 | 8/2009 | Haverkost et al. | |
| 7,582,100 B2 * | 9/2009 | Johnson | A61F 2/01 210/435 |
| 8,109,990 B2 | 2/2012 | Paul et al. | |
| 8,475,516 B2 | 7/2013 | Paul et al. | |
| 8,652,197 B2 | 2/2014 | Paul et al. | |
| 9,078,748 B2 | 6/2015 | Paul et al. | |
| 2001/0039450 A1 | 11/2001 | Pavcnik et al. | |
| 2003/0163159 A1 * | 8/2003 | Patel | A61F 2/01 606/200 |
| 2005/0187614 A1 | 8/2005 | Agnew | |
| 2005/0267513 A1 * | 12/2005 | Osborne | A61F 2/01 606/200 |
| 2006/0241675 A1 * | 10/2006 | Johnson | A61F 2/01 606/200 |
| 2007/0005095 A1 * | 1/2007 | Osborne | A61F 2/01 606/200 |
| 2007/0112423 A1 | 5/2007 | Chu | |
| 2008/0046071 A1 | 2/2008 | Pavcnik | |
| 2008/0140110 A1 | 6/2008 | Spence | |
| 2009/0234434 A1 | 9/2009 | Johnson et al. | |
| 2010/0217381 A1 | 8/2010 | Paul et al. | |
| 2012/0130476 A1 | 5/2012 | Paul et al. | |
| 2013/0289709 A1 | 10/2013 | Paul et al. | |
| 2014/0155987 A1 | 6/2014 | Paul et al. | |
| 2014/0309631 A1 | 10/2014 | McLawhorn et al. | |

OTHER PUBLICATIONS

Complete Prosecution History, U.S. Appl. No. 13/930,723, Compiled Feb. 6, 2014.
Complete Prosecution History, U.S. Pat. No. 8,475,516, Compiled Feb. 6, 2014.
Complete Prosecution History, U.S. Pat. No. 8,109,990, Compiled Feb. 6, 2014.
Volcano Corporation, "Crux: Vena Cava Filter," www.volcanocorp.com, Brochure, pp. 1-2, retrieved Aug. 26, 2014.
European Patent Office, Examination report dated Apr. 13, 2017 for European patent application No. 10706443.8.

* cited by examiner

LOW PROFILE INTRALUMINAL MEDICAL DEVICES

FIELD

The disclosure relates generally to the field of medical devices. More particularly, the disclosure relates to the field of medical devices suitable for use in body vessels.

BACKGROUND

A variety of expandable intraluminal medical devices have been developed over recent years. For example, stents are routinely used in several body lumens as a means for providing support to ailing vessels, such as coronary and non-coronary vessels. Occlusion devices are used to substantially block fluid flow through a body vessel, and prosthetic valves are used to regulate fluid flow through a body vessel. Both prosthetic heart valves and venous valves have been the subject of significant development efforts in recent years.

Expandable intraluminal medical devices are typically delivered to a point of treatment using a delivery system designed for percutaneous techniques. In a conventional procedure, a caregiver navigates the delivery system through one or more body vessels until the expandable intraluminal medical device, which is typically contained in a distal tip of the delivery system, is positioned at or near the desired point of treatment. Next, the caregiver deploys the expandable intraluminal medical device from the delivery system, either by removing a constraining force for self-expandable devices or by providing an expansive force for balloon-expandable devices. Once deployment is complete, the delivery system is removed from the body vessel, leaving the intraluminal medical device in an expanded configuration at the point of treatment. This delivery and deployment technique is largely conventional and is used for most types of expandable intraluminal medical devices, including stents, occluders, valves, and other types of devices.

During delivery, expandable intraluminal medical devices are maintained in a compressed or reduced-diameter configuration within the delivery system to ensure navigability of the delivery system through the body vessel. The navigability of the delivery system is directly related to its overall outer diameter. A relatively large diameter limits the ability of a delivery system to be navigated past curves, angles, side branch openings and other impediments, and also limits the ability of a delivery system to enter and/or be navigated through small diameter vessels.

Because the delivery system must carry the intraluminal medical device to the point of treatment in the body vessel, efforts to minimize the outer diameter of delivery systems are necessarily confined by the ability of the intraluminal medical device to be compressed. The material, construction, and configuration of the medical device can limit its ability to be compressed, which, in turn, limits the useable outer diameter of the delivery system that will ultimately be used with the device.

Some intraluminal medical devices, including some prosthetic valves and occluders, include graft and/or valve members that add to the bulk of the support frame included in the device, compounding the difficulty associated with increasing the compressibility of the device. A need continues, therefore, for improved low profile medical devices.

BRIEF SUMMARY OF EXAMPLE EMBODIMENTS

Several example low profile medical devices are described and illustrated herein. One example low profile intraluminal filter comprises a first wire member having first and second ends and defining a first arcuate path with a first curve disposed between the first and second ends, the first arcuate path comprising only a single sigmoidal curve; a second wire member having third and fourth ends and defining a second arcuate path with a second curve disposed between the third and fourth ends, the second arcuate path comprising only a single sigmoidal curve; a third wire member having fifth and sixth ends and defining a third arcuate path with a third curve disposed between the fifth and sixth ends; a first connector connecting the first, third and fifth ends; and a second connector connecting the second, fourth and sixth ends and spaced from the first connector on the lengthwise axis of the medical device. Substantially no portion of the medical device is disposed on a first transverse axis of the medical device opposite the first, third and fifth ends and substantially no portion of the medical device is disposed on a second transverse axis of the medical device opposite the second, fourth and sixth ends when the medical device is in said radially expanded configuration.

Another example low profile medical device comprises a first wire member having first and second ends and defining a first arcuate path with a first curve disposed between the first and second ends, the first arcuate path comprising only a single sigmoidal curve; a second wire member having third and fourth ends and defining a second arcuate path with a second curve disposed between the third and fourth ends, the second arcuate path comprising only a single sigmoidal curve; a first connector connecting the first and third ends; a second connector connecting the second and fourth ends and spaced from the first connector on the lengthwise axis of the medical device; and a third wire member extending from the first connector to the second connector and defining a third arcuate path with a third curve disposed between the third and fourth ends, the third arcuate path comprising only a single sigmoidal curve.

Another example low profile medical device comprises a first series of at least three wire members, each wire member of the first series of wire members defining first and second ends and an arcuate path comprising only a single sigmoidal curve; a second series of at least three wire members, each wire member of the second series of wire members defining first and second ends and an arcuate path comprising only a single sigmoidal curve; a first connector connecting the first ends of the wire members of the first and second series of wire members; and a second connector connecting the second ends of the wire members of the first and second series of wire members, the second connector spaced from the first connector on the lengthwise axis of the medical device.

Additional understanding of the claimed devices can be obtained by reviewing the description of example embodiments, below, with reference to the appended drawings.

DETAILED DESCRIPTION OF EXAMPLE EMBODIMENTS

The following detailed description and appended drawings describe and illustrate various exemplary embodiments of the invention. The description and drawings serve to enable one skilled in the art to make and use the inventive apparatuses, and are not intended to limit the scope of the invention or the protection sought in any manner.

Figures 1, 2, 3:
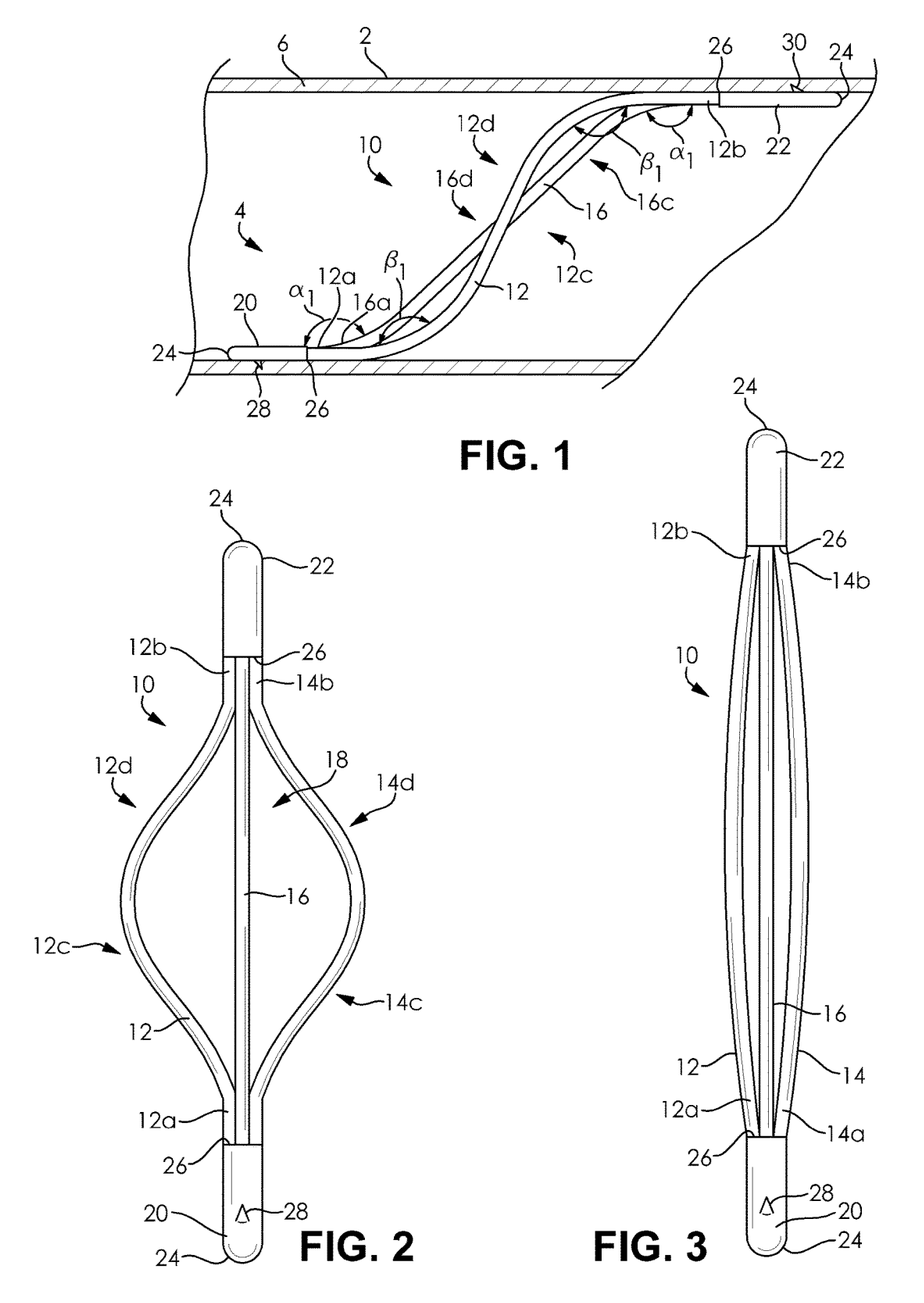
FIG. 1 is a sectional view of a body vessel with a first example medical device.
FIG. 2 is a top view of the first example medical device in an expanded configuration.
FIG. 3 is a top view of the first example medical device in a non-expanded configuration.

FIGS. 1, 2 and 3 illustrate a first example medical device 10. FIG. 1 illustrates the medical device 10 disposed within the lumen 4 defined by a vessel wall 6 of a body vessel 2. FIGS. 1 and 2 illustrate the medical device 10 in an expanded configuration; FIG. 3 illustrates the medical device 10 in a non-expanded configuration.

The medical device 10 includes first 12, second 14, and third 16 wire members. The first wire member 12 includes a first end 12a and a second end 12b. When the medical device 10 is in the expanded configuration, the wire member 12 defines an arcuate path 12c with a curve 12d disposed between the first 12a and second 12b ends. The arcuate path and curve of the first wire member of a medical device according to a particular embodiment can have any suitable size, shape and configuration. In the illustrated embodiment, the arcuate path 12c comprises only a single sigmoidal curve.

Similarly, the second wire member 14 includes first 14a and second 14b ends and, when the medical device 10 is in the expanded configuration, defines an arcuate path 14c that includes a curve 14d disposed between the ends 14a, 14b. The arcuate path and curve of the second wire member of a medical device according to a particular embodiment can have any suitable size, shape and configuration. In the illustrated embodiment, the arcuate path 14c has the same size, shape and configuration of the arcuate path 12c of the first wire member 12 and comprises only a single sigmoidal curve.

The first 12 and second 14 wire members cooperatively define a closed circumference 18. A first connector 20 is disposed at one end of the medical device 10 and a second connector 22 is disposed at the opposite end of the medical device 10. The first ends 12a, 14a of the first 12 and second wire 14 members are disposed within the first connector 20, and the second ends 12b, 14b of the first 12 and second 14 wire members are disposed in the second connector 22. Each of the connectors 20, 22 is attached to the appropriate ends 12a, 12b, 14a, 14b to maintain the closed circumference 18 defined by the wire members 12, 14. While the connectors 20, 22 are illustrated as hollow members that receive the ends 12a, 12b, 14a, 14b of the wire members 12, 14, it is understood that any suitable means for connecting wire members together can be used, including mechanical connections, such as crimping, adhesives, a connection formed by annealing or brazing, or any other suitable structure that provides a means for connecting wire members. Also, as noted below, one or both of the connectors 20, 22 can be integrally formed with one or both of the wire members 12, 14. The specific structure selected for the means for connecting the wire members in a support frame according to a particular embodiment of the invention will depend on various considerations, including the materials used in the wire members 12, 14.

The first 12 and second 14 wire members can have any suitable size, shape and configuration. Furthermore, the first 12 and second 14 wire members can have the same or different size, shape and configuration. In the embodiment illustrated in FIGS. 1, 2 and 3, the wire members 12, 14 each comprise a wire having a circular cross-sectional shape. Furthermore, the wire members 12, 14 have the same size, including the same length and diameter, and configuration. When the medical device 10 is in its expanded configuration within a body vessel, such as the body vessel 2 illustrated in FIG. 1, the first 12 and second 14 wire members conform to the inner surface of the vessel wall.

Figure 4A:
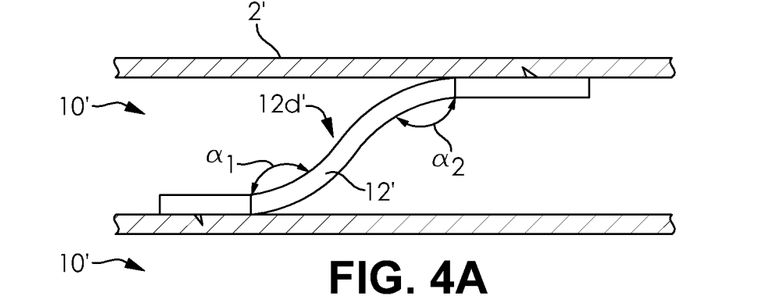
FIG. 4A is a sectional view of a body vessel with another alternative medical device.
Figure 4B:
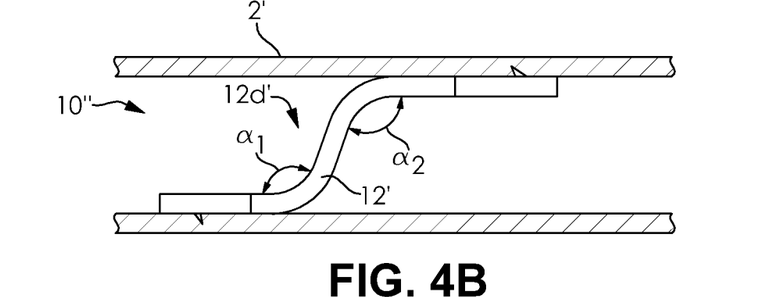
FIG. 4B is a sectional view of a body vessel with another alternative medical device.
Figure 4C:
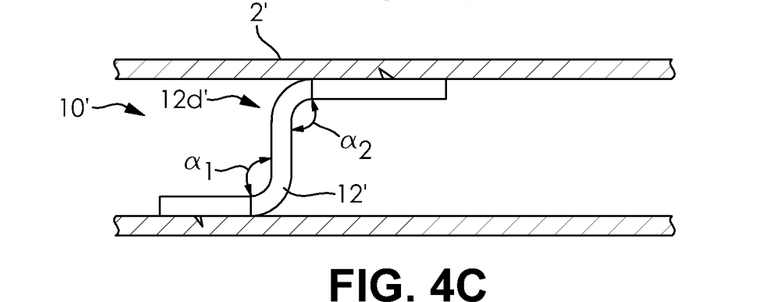
FIG. 4C is a sectional view of a body vessel with another alternative medical device.

Each of FIGS. 4A, 4B, 4C illustrates an alternative medical device 10' disposed within a body vessel 2'. In each of these figures, the first, second and third wire members of the illustrated medical device have the same configurations. As a result, the second and third wire members are not visible in each figure. These figures illustrate the effect of different angles in the curve of the wire members, providing a range of examples of suitable configurations of one or more wire members in a medical device according to an embodiment. FIG. 4A illustrates a first set of suitable inner angles $\alpha_1$, $\alpha_2$ of the curve 12d' of the first wire member 12'. FIG. 4B illustrates a first set of suitable inner angles $\alpha_1$, $\alpha_2$ of the curve 12d'. FIG. 4C illustrates a first set of suitable inner angles $\alpha_1$, $\alpha_2$ of the curve 12d'. Ranges of suitable angles for the inner angles of a curve defined by a wire member in a medical device according to an embodiment when the medical device is in an expanded configuration include an angle between about 90° and about 150, an angle between about 90° and about 135°, an angle between about 90° and about 120°, and an angle between about 90° and about 105°. As illustrated in FIGS. 4A, 4B and 4C, the inner angles can be selected to achieve a desired angle at which one or more wire members traverses the lumen of the body vessel when the medical device is in an expanded configuration within the body vessel.

The third wire member 16 extends from the first connector 20 to the second connector 22. As best illustrated in FIG. 2, the third wire member 16 in the illustrated embodiment spans the closed circumference 16 defined by the first 12 and second 14 wire members. The third wire member 16 includes a first end 16a and a second end 16b. When the medical device 10 is in the expanded configuration, the third wire member 16 defines an arcuate path 16c with a curve 16d disposed between the first 16a and second 16b ends.

The third wire member can be included in a medical device according to a particular embodiment for any suitable function. For example, a third wire member may provide a desired impact on the overall radial force of the medical device, particularly in embodiments in which the third wire member is formed of a different material that the first and second wire members. Also, inclusion of a third wire member can provide a desired imaging property to the medical device. For example, radiopacity of the medical device can be impacted by including a third wire member formed of platinum, gold or other radiopaque material. Also, inclusion of a third wire member can provide structural features for attaching additional components to the medical device, such as graft material or other components. Also, the third wire member could be coated with a medicament for localized drug elution. Also, inclusion of a third wire member can provide increased longitudinal stiffness/pushability for deployment of the medical device. Also, the third wire member in a medical device according to a particular embodiment could have a preset curvature to allow the medical device to better conform to and/or track a bend in body vessel or duct. In embodiments where the third wire member is not a conforming member, i.e., the third wire member doesn't conform to the vessel wall when the medical device is deployed within the lumen of a body vessel, the third wire member could provide a target for grasping and retrieval of the medical device. In these embodiments, the third wire member could be either metal or a biodegradable polymer that provides a limited window for retrieval before it goes away and leaves only the remainder of the medical device behind, including first and second wire members and the connectors. The third wire member in a medical device according to a particular embodiment could be made removable, allowing it to be retrieved while leaving the rest of the medical device behind.

The arcuate path and curve of the third wire member of a medical device according to a particular embodiment can have any suitable size, shape and configuration. In the illustrated embodiment, the arcuate path 16c comprises only a single sigmoidal curve. Furthermore, the arcuate path and curve of the third wire member of a medical device according to a particular embodiment can have the same or different size, shape and configuration of one or both of the first and second wire members of the medical device. In the illustrated embodiment, as best illustrated in FIG. 1, each of the first 12, second 14 and third 16 wire members have similar arcuate paths 12c, 14c, 16c and curves 12d, 14d, 16c in that each arcuate path 12c, 14c, 16c defines only a single sigmoidal curve. The sigmoidal curve 16d of the arcuate path 16c defined by the third wire member 16 is different from the sigmoidal curves 12d, 14d defined by the first 12 and second wire members 14, however, because the inner angles $\alpha_1$ of the curve 16d are greater than the inner angles $\beta_2$ of the curves 12d, 14d. As best illustrated in FIG. 1, a central portion 16e of the third wire member 16 traverses the lumen 4 of the body vessel 2 at a greater angle than the angle at which central portions 12e, 14e of the first 12 and second wire members traverse the lumen 4 of the body vessel 2 when the medical device 10 is in its expanded configuration. The inclusion of a third wire member 16 with this configuration is believed to enhance the overall radial strength of the medical device 10 without contributing significant bulk to the overall medical device 10. In a medical device according to a particular embodiment, the third wire member can conform to the inner surface of a body vessel within which the medical device is implanted, when the medical device is in its expanded configuration, or the third wire member can be a non-conforming wire member. As best illustrated in FIG. 1, the third wire member 16 of the illustrated medical device is a non-conforming wire member. In the illustrated embodiment, the third wire member 16 extends across the closed circumference 18 defined by the first 12 and second 14 wire members, effectively traversing the lumen 4 of the body vessel 2 when the medical device is in the expanded configuration.

Figure 5A:
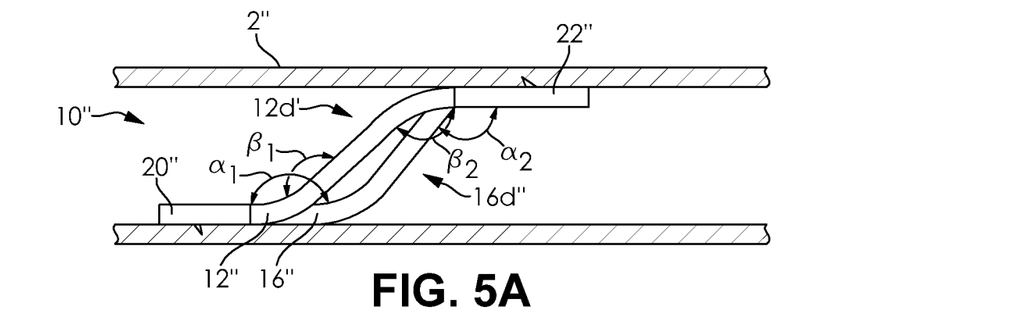
FIG. 5A is a sectional view of a body vessel with an alternative medical device.
Figure 5B:
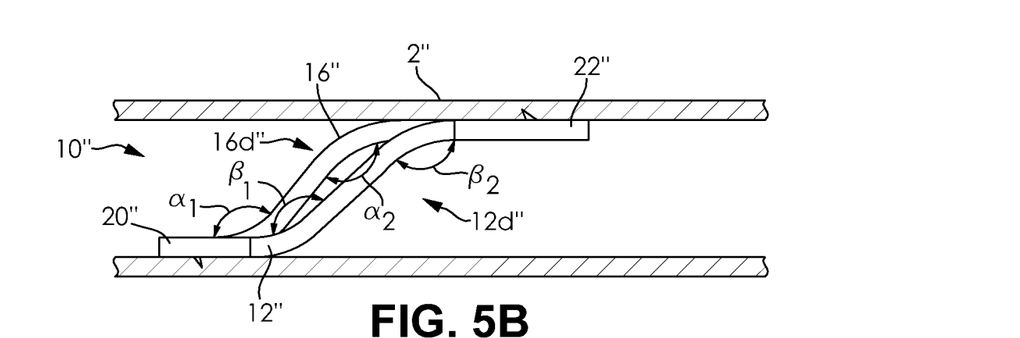
FIG. 5B is a sectional view of a body vessel with another alternative medical device.
Figure 5C:
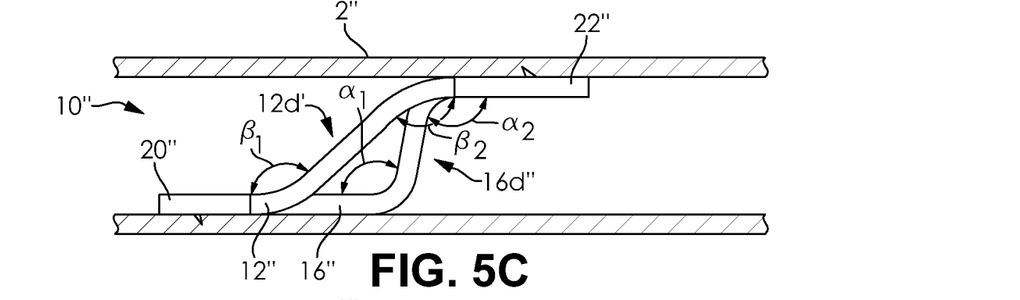
FIG. 5C is a sectional view of a body vessel with another alternative medical device.
Figure 5D:
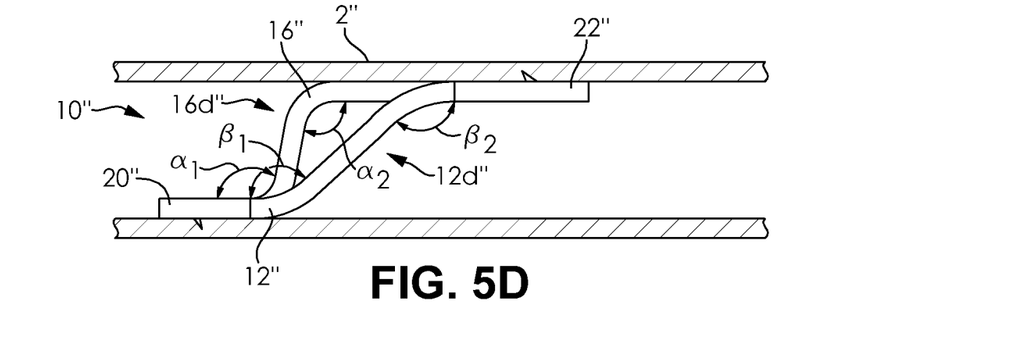
FIG. 5D is a sectional view of a body vessel with another alternative medical device.

Each of FIGS. 5A, 5B, 5C and 5D illustrate an alternative medical device 10" disposed within a body vessel 2". In each of these figures, the first and second wire members of the illustrated medical device have the same configurations. As a result, the second wire member is not visible in each figure. Also, the third wire member of the medical device in each figure has a different configuration relative to the first and second wire members of the illustrated medical device, providing a range of examples of suitable configurations of the third wire member relative to the first and second wire members. In FIGS. 5A and 5B, the inner angles $\alpha_1$, $\alpha_2$ of the curve 16d" are greater than the inner angles $\beta_1$, $\beta_2$ of the curves 12d". In contrast, in FIGS. 5C and 5D, the inner angles $\alpha_1$, $\alpha_2$ of the curve 16d" are less than the inner angles $\beta_1$, $\beta_2$ of the curves 12d". Also, in FIGS. 5A and 5C, the curve 16d" of the third wire member 16" is generally concave with respect to the curve 12" of the first wire member 12", such that the curve 16d" is largely disposed on the opposite side of the first wire member 12" from the first connector 20". In contrast, in FIGS. 5B and 5D, the curve 16d" of the third wire member 16" is generally convex with respect to the curve 12" of the first wire member 12", such that the curve 16d" is largely disposed on the same side of the first wire member 12" from the first connector 20".

The third wire member 16 can have any suitable size, shape and configuration. Furthermore, the third wire member 16 can have the same or different size, shape and configuration as one or both of the first 12 and second 14 wire members. In the embodiment illustrated in FIGS. 1, 2 and 3, the third wire member 16 comprises a wire having a circular cross-sectional shape. Furthermore, the wire member 16 has the same size, including the same length and diameter, of the first 12 and second 14 wire members.

It is noted that, while the medical device 10 is illustrated as being formed of independent wire members 12, 14, 16 connected to each other, a medical device according to an embodiment can be formed of a unitary piece of material using suitable techniques and materials. For example, a medical device could be cut from a tube of shape memory material using conventional or other suitable techniques. For example, a medical device could be cut from a tube of nitinol using laser cutting or other suitable techniques, followed by expansion and heat treatment steps that are known in the art. In these unitary embodiments, the wire members comprise struts in the resulting structure and the connectors comprise joints at which individual struts are joined to each other. Connectors that are separate and distinct from the struts are not necessary in these embodiments—the joints perform the connecting function of the connectors in these embodiments. Also, a single wire member could be used to form a medical device using suitable bending techniques. In these embodiments, bends in the wire member eliminate the need for connectors. It is noted, though, that in these embodiments, the inclusion of one or more connectors might still be considered advantageous as a crimping force providing by the connector may maintain a bend in the single wire member in a minimal thickness. It is also noted that a single wire member having one end formed by a bend and the other end formed by attaching two independent ends of the single wire member can be used to form the support frame.

In the illustrated embodiment, each connector 20, 22 includes a closed 24 and an open 26 end. The open end 26 is sized and configured to receive the appropriate ends 12a, 12b, 14a, 14b, 16a, 16b of the wire member 12, 14, 16. The closed end 24 does not provide access to the inside of the connector 20, 22. A barb is advantageously included on each of the connectors 20, 22. In this embodiment, the barb 28 on the first connector 20 is disposed on a surface of the first connector 20 that faces in a substantially opposite direction than the direction faced by the surface of the second connector 22 on which barb 30 is disposed, relative to a plane containing the closed circumference 16 defined by the wire members 12, 14. Also in this embodiment, the first barb 28 extends away from the first connector 20 in a direction that is different from the direction in which the second barb 30 extends away from the second connector 22. As best illustrated in FIG. 1, the barbs 28, 30 advantageously extend away from the respective connector 20, 22 in substantially opposite directions. This configuration is expected to provide advantageous anchoring characteristics for the medical device 10. Any suitable orientation for barbs can be used, however, when included in a medical device according to a particular embodiment. It is noted that the barbs 28, 30 in the illustrated embodiment are not necessarily drawn to scale relative to any other component and/or element of the medical device 10, and are shown as relatively large elements for illustrative purposes only.

Figure 6:
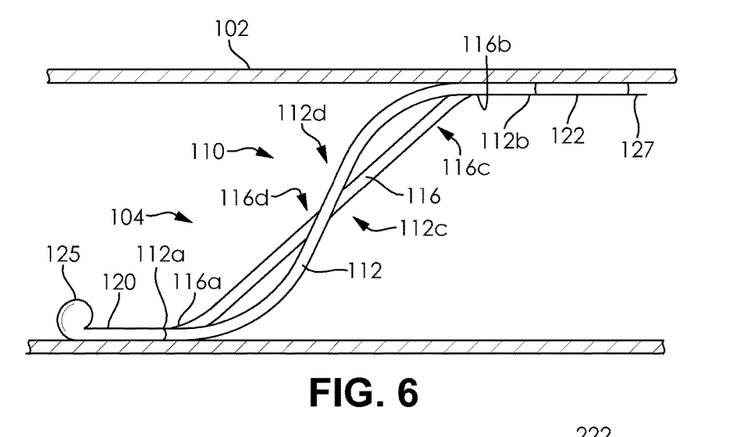
FIG. 6 is a sectional view of a body vessel with a second example medical device.

Medical devices according to particular embodiments can include additional structural features. For example, FIG. 6 illustrates another example medical device 110 that includes structural features that enable retrieval of the device 110 from a location within the lumen 104 of a body vessel 102. The medical device 110 is similar to the medical device 10 illustrated in FIGS. 1 through 3 and described above, except as indicated below. Thus, the medical device 110 includes first 112, second (not visible in FIG. 6), and third 116 wire members. The first wire member 112 includes a first end 112a and a second end 112b. When the medical device 110 is in the expanded configuration, the wire member 112 defines an arcuate path 112c with a curve 112d disposed between the first 112a and second 112b ends. The arcuate path 112c comprises only a single sigmoidal curve. The second wire member includes first and second ends and, when the medical device 110 is in the expanded configuration, defines an arcuate path that includes a curve disposed between the ends. The arcuate path has the same size, shape and configuration of the arcuate path 112c of the first wire member 112 and comprises only a single sigmoidal curve. A first connector 120 is disposed at one end of the medical device 110 and a second connector 122 is disposed at the opposite end of the medical device 110. The first ends 112a, 114a of the first 112 and second wire members are disposed within the first connector 120, and the second ends 112b, 114b of the first 112 and second wire members are disposed in the second connector 122. Each of the connectors 120, 122 is attached to the appropriate ends 112a, 112b to maintain the closed circumference 116 defined by the wire members.

In this embodiment, the first connector 120 provides an inwardly-directed projection 125 on its end. The inwardly-directed projection 125 has a rounded or ball shape. Any suitable structure can be included to facilitate retrieval. For example, in the illustrated embodiment, the second connector 122 provides a tab member that defines a loop 127, which is also considered suitable. Each of these structures, and others with suitable shapes and configurations, can be used to engage the medical device with a suitable retrieval device capable of grasping the inwardly-directed projection 125, 127, such as a snare, grasper, or other suitable retrieval device. Furthermore, while the illustrated medical device 110 includes two structures 125, 127 for facilitating retrieval, a medical device according to a particular embodiment can have only a single structure disposed on one of the connectors 120, 122.

FIGS. 7, 8, 9A and 10 illustrate another example medical device 210 that includes an additional wire member 217 that extends from the first connector 220 to the second connector 222. The medical device 210 is similar to the medical device 10 illustrated in FIGS. 1 through 3 and described above, except as indicated below. Thus, the medical device 210 includes first 212, second 214, and third 216 wire members, in addition to the fourth wire member 217, which is described in detail below. The first wire member 212 includes a first end 212a and a second end 212b. When the medical device 210 is in the expanded configuration, the wire member 212 defines an arcuate path 212c with a curve 212d disposed between the first 212a and second 212b ends. The arcuate path 212c comprises only a single sigmoidal curve. The second wire member 214 includes first 214a and second 214b ends and, when the medical device 210 is in the expanded configuration, defines an arcuate path 214c that includes a curve 214d disposed between the ends. The arcuate path 214c has the same size, shape and configuration of the arcuate path 212c of the first wire member 212 and comprises only a single sigmoidal curve. A first connector 220 is disposed at one end of the medical device 210 and a second connector 222 is disposed at the opposite end of the medical device 210. The first ends 212a, 214a of the first 212 and second wire members are disposed within the first connector 220, and the second ends 212b, 214b of the first 212 and second wire members are disposed in the second connector 222. Each of the connectors 220, 222 is attached to the appropriate ends 212a, 212b to maintain the closed circumference 216 defined by the wire members.

Figures 7, 8, 9A, 9B, 9C:
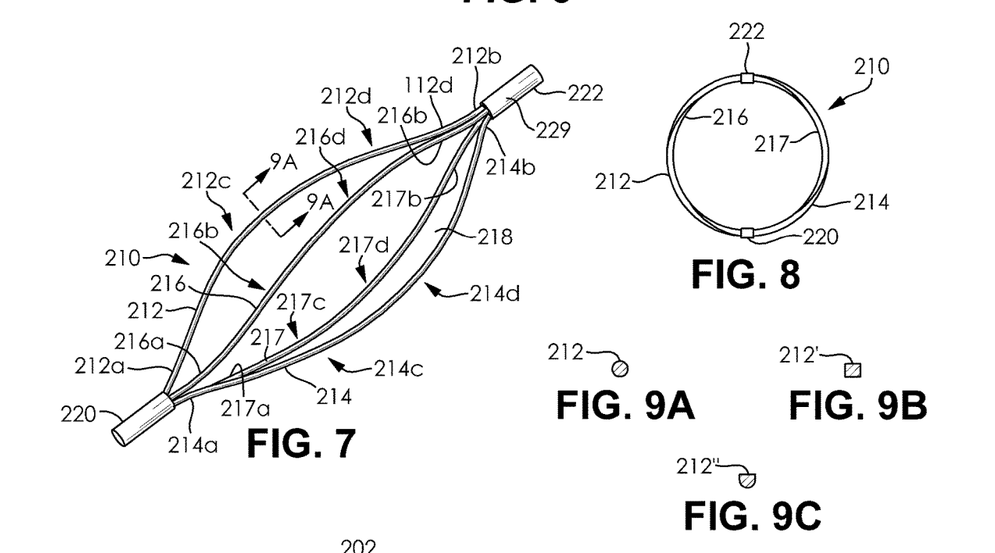
FIG. 7 is a perspective view of a third example medical device.
FIG. 8 is an end view of the third example medical device.
FIG. 9A is an enlarged sectional view of a wire member of the third example medical device, taken along line 9A-9A in FIG. 7.
FIG. 9B is an enlarged sectional view of an alternative wire member.
FIG. 9C is an enlarged sectional view of an alternative wire member.

As best illustrated in FIG. 7, the third 216 and fourth 217 wire members span the closed circumference 218 defined by the first 212 and second 214 wire members. The third wire member 216 includes a first end 216a and a second end 216b. When the medical device 210 is in the expanded configuration, the third wire member 216 defines an arcuate path 216c with a curve 216d disposed between the first 216a and second 216b ends. Similarly, the fourth wire member 217 includes a first end 217a and a second end 217b. When the medical device 210 is in the expanded configuration, the fourth wire member 217 defines an arcuate path 217c with a curve 217d disposed between the first 217a and second 217b ends. In this embodiment, all wire members 212, 214, 216, 217 are conforming wire members, as best illustrated in FIG. 10.

The arcuate path and curve of the third and fourth wire members of a medical device according to a particular embodiment can have any suitable size, shape and configuration. In the illustrated embodiment, the arcuate paths 216c, 217c comprises only a single sigmoidal curve. Furthermore, the arcuate paths and curves of the third and fourth wire members of a medical device according to a particular embodiment can have the same or different size, shape and configuration of one or both of the first and second wire members of the medical device. In the illustrated embodiment, as best illustrated in FIG. 7, each of the first 212, second 214, third 216 and fourth 217 wire members have similar arcuate paths 212c, 214c, 216c, 217c and curves 212d, 214d, 216c, 217d in that each arcuate path 212c, 214c, 216c, 217c defines only a single sigmoidal curve. Also in this embodiment, the third 216 and fourth 217 wire members have the same diameter as the first 212 and second 214 wire members.

Figure 10:
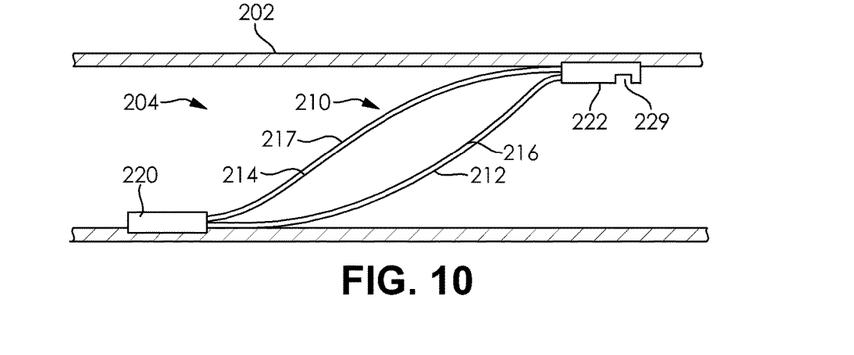
FIG. 10 is a sectional view of a body vessel with the third example medical device.
Figure 11:
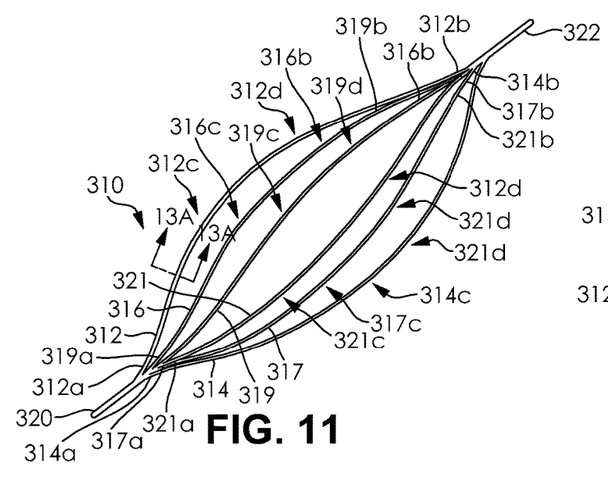
FIG. 11 is a perspective view of a fourth example medical device.
Figure 12:
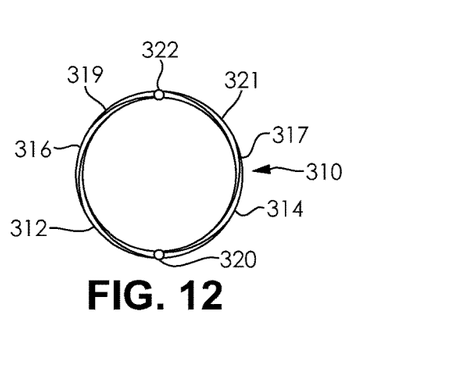
FIG. 12 is an end view of the fourth example medical device.

As best illustrated in FIG. 10, this configuration places portions of two of the wire members 212, 216 in a substantially parallel arrangement on one side of the medical device 210 when the medical device 210 is in its expanded configuration within a lumen 204 of a body vessel 202. The other wire members 214, 217 are placed in a similar arrangement on the opposite side of the medical device 210.

Also in this embodiment, the connector 222 defines a notch 229 suitable for use with a retrieval device for removing the medical device 210 from a location within a body vessel. The notch 229 is an alternative to the inwardly-directed protrusion structures described above and illustrated in FIG. 6.

In all embodiments, all wire members can have any suitable configuration. For example, the wire members can be formed from one or more lengths of wire or can be cut from a solid tubular section of material. Furthermore, the wire members can have any suitable cross-sectional shape. As best illustrated in FIG. 9A, the wire member 212, indeed all wire members in the illustrated embodiment, have a generally circular cross-sectional shape. Other examples of suitable cross sectional shapes include a generally square cross sectional shape, such as the alternative wire member 212' illustrated in FIG. 9B, a generally D-shaped cross-section shape, such as the alternative wire member 212" illustrated in FIG. 9C, a generally triangular cross-sectional shape, a generally ovoid cross-sectional shape, and a generally rectangular cross-sectional shape.

FIGS. 11, 12, 13A and 14 illustrate another example medical device 310 that includes an additional pair of wire members 317, 319, each of which extends from the first connector 320 to the second connector 322. The medical device 310 is similar to the medical device 10 illustrated in FIGS. 1 through 3 and described above, except as indicated below. Thus, the medical device 310 includes first 312, second 314, third 316 and fourth 317 wire members, in addition to the fifth 319 and sixth 321 wire members, which are described in detail below. The first wire member 312 includes a first end 312a and a second end 312b. When the medical device 310 is in the expanded configuration, the wire member 312 defines an arcuate path 312c with a curve 312d disposed between the first 312a and second 312b ends. The arcuate path 312c comprises only a single sigmoidal curve. The second wire member 314 includes first 314a and second 314b ends and, when the medical device 310 is in the expanded configuration, defines an arcuate path 314c that includes a curve 314d disposed between the ends. The arcuate path 314c has the same size, shape and configuration of the arcuate path 312c of the first wire member 312 and comprises only a single sigmoidal curve. A first connector 320 is disposed at one end of the medical device 310 and a second connector 322 is disposed at the opposite end of the medical device 310. The first ends 312a, 314a of the first 312 and second 314 wire members are disposed within the first connector 320, and the second ends 312b, 314b of the first 312 and second 314 wire members are disposed in the second connector 322. Each of the connectors 320, 322 is attached to the appropriate ends 312a, 312b to maintain the closed circumference 318 defined by the wire members. In this embodiment, the medical device 310 is formed as a unitary device cut from a section of a tube, such as a tube of nickel titanium alloy. As such, all wire members and both connectors are integral with each other. Furthermore, in this embodiment, all wire members are conforming members.

Figure 14:
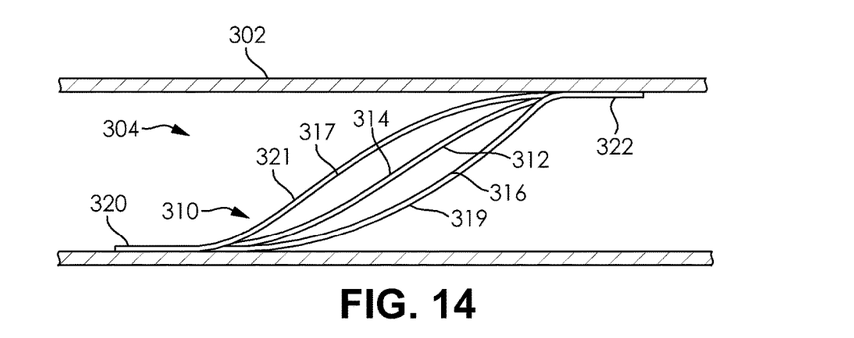
FIG. 14 is a sectional view of a body vessel with the fourth example medical device.

As best illustrated in FIG. 14, the third 316 and fourth 317 wire members closely follow the path of the first 312 and second 314 wire members when the medical device 310 is in the expanded configuration. The third wire member 316 includes a first end 316a and a second end 316b. When the medical device 310 is in the expanded configuration, the third wire member 316 defines an arcuate path 316c with a curve 316d disposed between the first 316a and second 316b ends. Similarly, the fourth wire member 317 includes a first end 317a and a second end 317b. When the medical device 310 is in the expanded configuration, the fourth wire member 317 defines an arcuate path 317c with a curve 317d disposed between the first 317a and second 317b ends.

Similarly, the fifth 319 and sixth 321 wire members closely follow the path of the first 312 and second 314 wire members when the medical device 310 is in the expanded configuration. The fifth wire member 319 includes a first end 319a and a second end 319b. When the medical device 310 is in the expanded configuration, the fifth wire member 319 defines an arcuate path 319c with a curve 319d disposed between the first 319a and second 319b ends. Similarly, the sixth wire member 321 includes a first end 321a and a second end 321b. When the medical device 310 is in the expanded configuration, the sixth wire member 321 defines an arcuate path 321c with a curve 321d disposed between the first 321a and second 321b ends.

The arcuate path and curve of the third, fourth, fifth and sixth wire members of a medical device according to a particular embodiment can have any suitable size, shape and configuration. In the illustrated embodiment, the arcuate paths 316c, 317c, 319c, 321c comprises only a single sigmoidal curve. Furthermore, the arcuate paths and curves of the third, fourth, fifth and sixth wire members of a medical device according to a particular embodiment can have the same or different size, shape and configuration of one or both of the first and second wire members of the medical device. In the illustrated embodiment, as best illustrated in FIG. 7, each of the first 312, second 314, third 316, fourth 317, fifth 319 and sixth 321 wire members have similar arcuate paths 312c, 314c, 316c, 317c, 319c, 321c and curves 312*d*, 314*d*, 316*c*, 317*d*, 319*d*, 321*d* in that each arcuate path 312*c*, 314*c*, 316*c*, 317*c*, 319*c*, 321*c* defines only a single sigmoidal curve.

Also in this embodiment, while not discernable in the Figures, each of the third 316, fourth 317, fifth 319 and sixth 321 wire members have the same diameter. Furthermore, the diameter of these wire members 316, 317, 319, 321 is less than the diameter of the first 312 and second 314 wire members.

As best illustrated in FIG. 14, this configuration places portions of three of the wire members 312, 316, 319 in a substantially parallel arrangement on one side of the medical device 310 when the medical device 310 is in its expanded configuration within a lumen 304 of a body vessel 302. The other wire members 314, 317, 321 are placed in a similar arrangement on the opposite side of the medical device 310. This configuration, including the relative diameters of the wire members 312, 316, 319, provides a balanced approach between a desire to add additional structure to the medical device 310 and a desire to maintain its low profile nature.

Figure 13A:
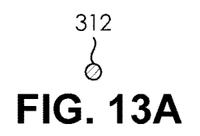
FIG. 13A is an enlarged sectional view of a wire member of the fourth example medical device, taken along line 13A-13A in FIG. 11.
Figure 13B:
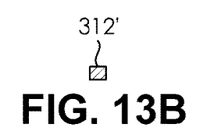
FIG. 13B is an enlarged sectional view of an alternative wire member.
Figure 13C:
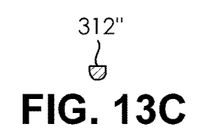
FIG. 13C is an enlarged sectional view of an alternative wire member.

Just as with medical devices with wire members formed from lengths of wire, a medical device that is formed from a section of a tube according to an embodiment can include wire members with any suitable cross-sectional shape. As best illustrated in FIG. 13A, the wire member 312, indeed all wire members in the illustrated embodiment, have a generally circular cross-sectional shape. Other examples of suitable cross sectional shapes include a generally square cross sectional shape, such as the alternative wire member 312' illustrated in FIG. 13B, a generally D-shaped cross-section shape, such as the alternative wire member 312" illustrated in FIG. 13C, a generally triangular cross-sectional shape, a generally ovoid cross-sectional shape, and a generally rectangular cross-sectional shape.

Figures 15, 16:
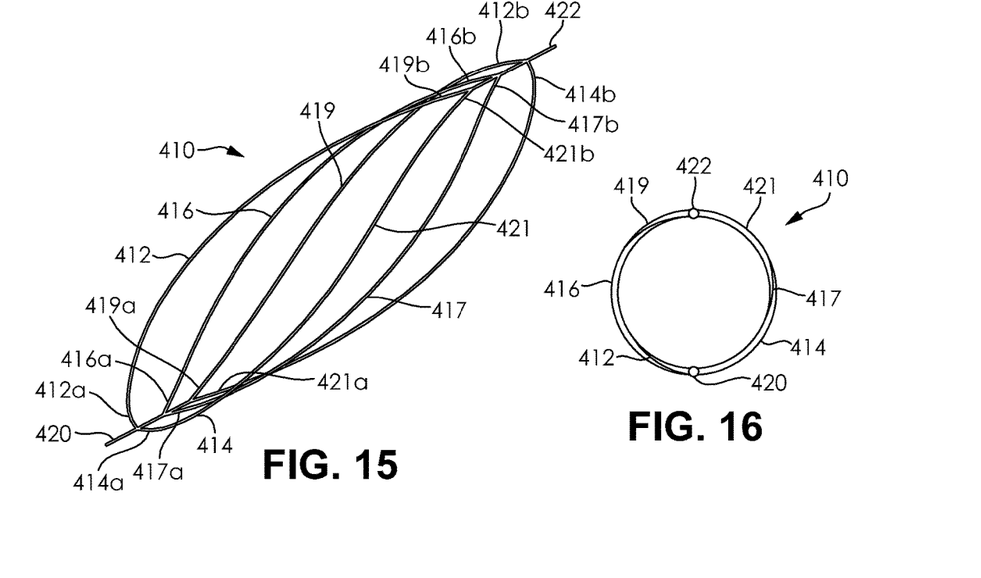
FIG. 15 is a perspective view of a fifth example medical device.
FIG. 16 is an end view of the fifth example medical device.

FIGS. 15 and 16 illustrate another example medical device 410. The medical device 410 is similar to the medical device 310 illustrated in FIGS. 11, 12 13A and 14, and described above, except as indicated below. Thus, the medical device 410 includes first 412, second 414, third 416, fourth 417, fifth 419, and sixth 421 wire members. The wire member 412, 414, 416, 417, 419, 421 have the same portions as those described above for medical device 310 and, for simplicity and clarity, are not described in detail or referenced individually for this embodiment. Also similar to medical device 310, the medical device 410 is formed as a unitary device cut from a section of a tube. As such, all wire members and both connectors are integral with each other. Furthermore, in this embodiment, all wire members are conforming members.

In this embodiment, the first ends 412*a*, 414*a*, 416*a*, 417*a*, 419*a*, 421*a* and second ends 412*b*, 414*b*, 416*b*, 417*b*, 419*b*, 421*b* of each of the wire members 412, 414, 416, 417, 419, 421 interfaces with the respective connector 420, 422 and a point spaced from the points at which the other first ends 412*a*, 414*a*, 416*a*, 417*a*, 419*a*, 421*a* and second ends 412*b*, 414*b*, 416*b*, 417*b*, 419*b*, 421*b* interface with the respective connector 420, 422, providing spaced interfaces along the lengths of each of the connectors 420, 422.

In the embodiment illustrated in FIGS. 15 and 16, pairs of ends of wire members interface with a connector at the same point on the axial length of the connector. For example, as best illustrated in FIG. 15, second end 412*b* of wire member 412 and second end 414*b* of wire member 414 interface with connector 422 at opposing sides of connector 422 but at the same point on the axial length of the connector. In the illustrated embodiment, opposing pairs of the first ends 412*a*, 414*a*, 416*a*, 417*a*, 419*a*, 421*a* and opposing pairs of the second ends 412*b*, 414*b*, 416*b*, 417*b*, 419*b*, 421*b* of the wire members 412, 414, 416, 417, 419, 421 interface with one of the connectors 420, 422 at the same point on the axial length of the connector 420, 422.

Figure 17:
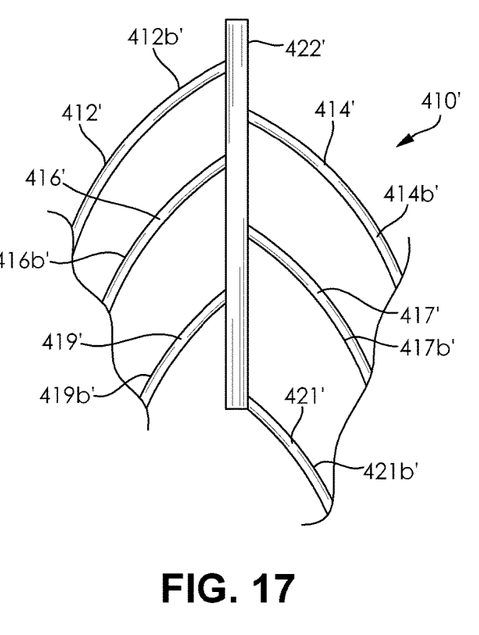
FIG. 17 is a partial perspective view of an alternative medical device.

It is noted, though, that in a medical device according to an embodiment, one or more opposing pairs of ends of the wire members can interface with one of the connectors at different points on the axial length of the respective connector, providing a staggered arrangement along the length of the connector. FIG. 17 illustrates a medical device 410' according to an alternative embodiment with this arrangement. In this embodiment, an opposing pair of second ends 412*b*', 414*b*' interface with connector 422' at different points on the axial length of the connector 422'. Similarly, an opposing pair of second ends 416*b*', 417*b*' and an opposing pair of second ends 419*b*' and 421*b*' interface with connector 422' at different points on the axial length of the connector 422'. Overall, this provides a staggered arrangement of interfaces between the ends 412*b*', 414*b*', 416*b*', 417*b*', 419*b*', 421*b*' of the members 412', 414', 416', 417', 419', 421'. While not illustrated in the Figure, the first ends of the wire members 412', 414', 416', 417', 419', 421' can interface with the other connector at the opposite end of the medical device 410' in a similar staggered arrangement. Alternatively, the first ends can interface with the other connector in another arrangement, such as the arrangement described above for medical device 410 and best illustrated in FIG. 15.

Figure 17A:
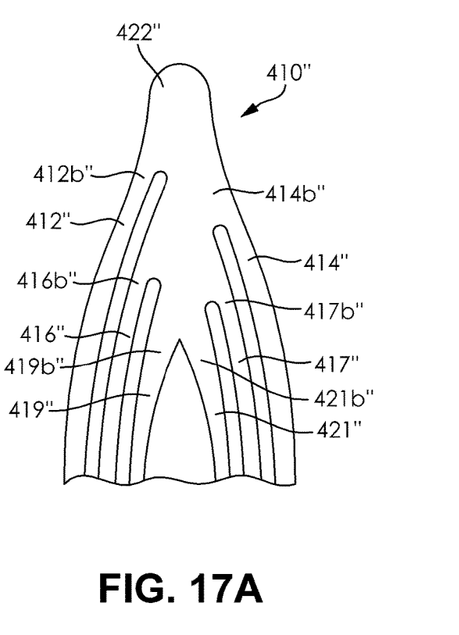
FIG. 17A is a partial perspective view of another alternative medical device.

FIG. 17A illustrates a medical device 410" according to another alternative embodiment with a staggered arrangement of opposing ends of the wire members. In this embodiment, an opposing pair of second ends 412*b*", 414*b*" interface with connector 422" at different points on the axial length of the connector 422". Similarly, an opposing pair of second ends 416*b*", 417*b*" and an opposing pair of second ends 419*b*" and 421*b*" interface with connector 422" at different points on the axial length of the connector 422". Overall, this provides a staggered arrangement of interfaces between the ends 412*b*", 414*b*", 416*b*", 417*b*", 419*b*", 421*b*" of the members 412", 414", 416", 417", 419", 421". While not illustrated in the Figure, the first ends of the wire members 412", 414", 416", 417", 419", 421" can interface with the other connector at the opposite end of the medical device 410" in a similar staggered arrangement. Alternatively, the first ends can interface with the other connector in another arrangement, such as the arrangement described above for medical device 410 and best illustrated in FIG. 15.

Methods of placing multiple medical devices within a body vessel are also contemplated. In example methods, multiple medical devices, each comprising a medical device in accordance with an embodiment of the invention, such as any of the embodiments described herein, are deployed from a delivery system into the lumen of a body vessel. In the example methods, conventional delivery systems appropriate for the particular medical device being deployed can be used. The medical devices are deployed, however, at particular orientations relative each other.

Figure 18A:
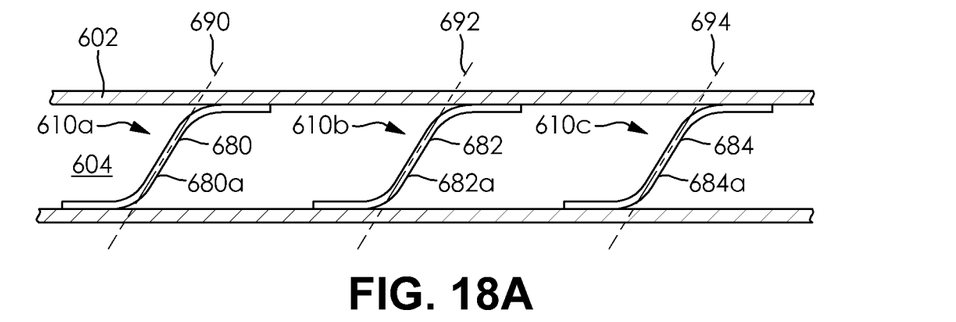
FIG. 18A is a sectional view of a body vessel with a plurality of example medical devices.
Figure 18B:
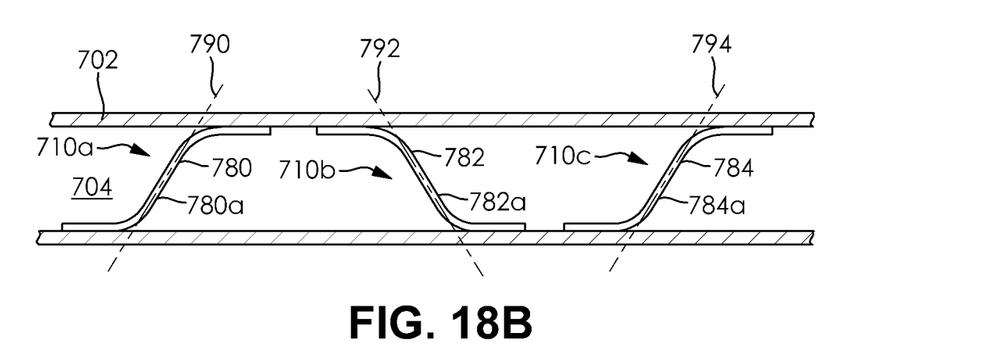
FIG. 18B is a sectional view of a body vessel with a plurality of example medical devices.
Figure 18C:
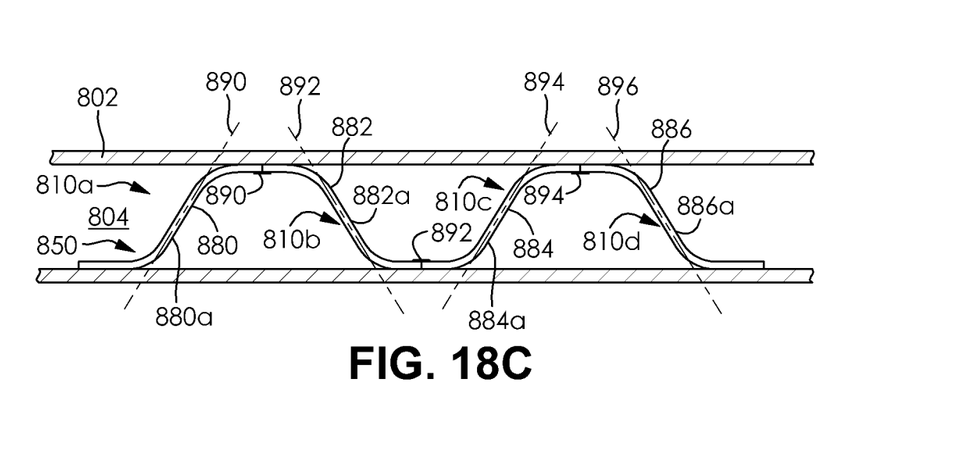
FIG. 18C is a sectional view of a body vessel with a plurality of example medical devices.

Each of FIGS. 18A, 18B, and 18C illustrates a body vessel within which a plurality of medical devices has been placed. FIG. 11A illustrates a body vessel 602 following placement of three medical devices 610*a*, 610*b*, 610*c* into the lumen 604 of the body vessel 602 according to a first example method. This example method comprises deploying multiple medical devices into a body vessel such that at least a portion 680*a* of one wire member 680 from a first medical device 610*a* lies on a first plane 690 and at least a portion 682*a* of one wire member 682 from a second medical device 610*b* lies on a second plane 692, and such that the planes 690, 692 transect the body vessel 602 and are substantially parallel to each other. A third medical device 610c can be placed within the body vessel 602 such that at least a portion 684a of one wire member 684 from the third medical device 610c lies on a third plane 694 that transects the body vessel 602 and is substantially parallel to the first 690 and second 692 planes. Indeed, a method according to an embodiment can include deploying any suitable number of medical devices according to embodiments of the invention such that at least a portion of one wire member from the medical device lies on a plane that transects the body vessel 602 and is substantially parallel to the first 690 and second 692 planes.

FIG. 18B illustrates a body vessel 702 following placement of three medical devices 710a, 710b, 710c into the lumen 704 of the body vessel 702 according to another example method. This example method comprises deploying multiple medical devices into a body vessel such that at least a portion 780a of one wire member 780 from a first medical device 710a lies on a first plane 790 and at least a portion 782a of one wire member 782 from a second medical device 710b lies on a second plane 792, and such that the planes 790, 792 transect the body vessel 702 and transect each other. A third medical device 710c can be placed within the body vessel 702 such that at least a portion 784a of one wire member 784 from the third medical device 710c lies on a third plane 794 that transects the body vessel 702 and is substantially parallel to the first 790 plane and transects the second 792 plane. Indeed, a method according to an embodiment can include deploying any suitable number of medical devices according to embodiments of the invention such that at least a portion of one wire member from the medical device lies on a plane that transects the body vessel 702 and that either is substantially parallel to the first 790 plane and transects the second 792 plane or transects the first plane 790 and is substantially parallel to the second plane 792.

FIG. 18C illustrates a body vessel 802 following placement of four connected medical devices 810a, 810b, 810c, 810d into the lumen 804 of the body vessel 802 according to another example method. As illustrated in the Figure, the adjacent pairs of the medical devices 810a, 810b, 810c, 810d are connected to each other such that the four medical devices 810a, 810b, 810c, 810d form a medical device assembly 850. This example method comprises deploying multiple connected medical devices into a body vessel such that at least a portion 880a of one wire member 880 from a first medical device 810a lies on a first plane 890 and at least a portion 882a of one wire member 882 from a second medical device 810b lies on a second plane 892, and such that the planes 890, 892 transect the body vessel 802 and transect each other. A third medical device 810c is placed within the body vessel 802 such that at least a portion 884a of one wire member 884 from the third medical device 810c lies on a third plane 894 that transects the body vessel 802 and is substantially parallel to the first 890 plane and transects the second 892 plane. A fourth medical device 810d is placed within the body vessel 802 such that at least a portion 886a of one wire member 886 from the fourth medical device 810d lies on a fourth plane 896 that transects the body vessel 802 and is substantially parallel to the second 892 plane and transects the third 894 plane. Indeed, a method according to an embodiment can include deploying any suitable number of connected medical devices according to embodiments of the invention such that at least a portion of one wire member from the medical device lies on a plane that transects the body vessel 802 and that either is substantially parallel to the first 890 plane and transects the second 892 plane or transects the first plane 890 and is substantially parallel to the second plane 892. Examples of suitable numbers of connected medical devices include two, three, four, five, six, ten, and twelve connected medical devices.

In this example method, the medical devices 810a, 810b, 810c, 810d can be connected to each other in any suitable manner, including being integrally formed with each other, being mechanically connected to each other, such as with a separate connector, clip, or other connector member (illustrated in FIG. 18C as connector members 890, 892 and 894), being adhered to each other, and being fused with each other. As an example, each of the medical devices can include one or more sections of cannula secured to one or more of the wire members or the connectors of the medical device. An elongate rod, such as an elongate section of stainless steel or other suitable material, can be passed through one or more cannula on each of the medical devices to secure the medical devices to each other and form a medical device assembly. This structure can be repeated, if desired, with additional cannulae on each medical device and inclusion of one or more additional elongate rods. The elongate rods can be fixedly attached to the cannulae on the medical devices, such as with a weld joint or an adhesive to permanently secure the medical devices to each other. Alternatively, the rods can be temporarily secured to the cannulae, such as with a relatively weak adhesive or a bioabsorable material, such that the rods can be removed after an appropriate period of time. Also alternatively, the rods can simply be passed through the cannulae without being attached to the cannulae other than through the mechanical engagement of a rod being passed through a passageway. In these embodiments, the connections between medical devices, such as medical devices 810a, 810b, 810c, 810d, can be formed prior to placement in a suitable delivery system, after placement within a suitable delivery system, or even after placement within a body vessel. Furthermore, the connections between all adjacent pairs of medical devices in a medical device assembly can be the same or different types of connections can be used.

In all embodiments, the wire members can be formed of any suitable resilient material acceptable for use in implantable medical devices. Examples of suitable materials include, but are not limited to, stainless steel, nitinol, nickel-cobalt-chromium alloys, nickel-cobalt-chromium-molybdenum alloys, polymeric materials, and other biocompatible materials. Nickel-cobalt-chromium-molybdenum alloys, such as MP35N (Carpenter Technology, Wyomissing, Pa.; MP35N is a registered trademark of SPS Technologies, Inc.), are considered particularly advantageous at least because of the relatively high tensile strength provided by these materials. As used herein, the term "wire member" does not refer to any particular size, diameter, or cross-sectional shape. While wire members having substantially circular cross-sectional shapes offer particular advantages, they are not required. Examples of other suitable cross-sectional shapes include, but are not limited to, flat, square, triangular, D-shaped, trapezoidal, and delta-shaped cross-sectional shapes. Also, as mentioned above, a medical device according to an embodiment can comprise a unitary member cut from an appropriate material, such as from a tube of shape memory material. In these embodiments, the wire members comprise struts in the structure resulting from the cutting process.

Also, the connectors in all embodiments can be formed from the same material or a different material than that of the wire members. Skilled artisans will be able to select appropriate materials for use in a support frame according to a particular embodiment of the invention based on various considerations, including the intended use, treatment environment and manufacturing demands of the medical device. The inventors have determined that wire members formed of nitinol and connectors formed of stainless steel provide a medical device with desirable characteristics for use in a variety of applications, including as a component in intraluminal medical devices, such as stents, prosthetic valves, and occluders.

While the medical devices described herein are considered useful independent of additional components, as an intraluminal stent, for example, the frames are also useful as a platform onto which other components and or functionalities can be added to provide new and useful intraluminal medical devices of various types, such as stents, prosthetic valves, occluders, filters, and the like. Various examples of such devices are described below.

While various embodiments are described with reference to specific features of particular drawings, it is understood that the various elements and/or features described herein in connection with one particular embodiment can be combined with those of another without departing from the scope of the invention. Furthermore, the embodiments described and illustrated herein represent examples selected by the inventors for the purpose of describing the invention; they are not intended to limit the scope of the invention in any manner. Rather, they serve only to aid those skilled in the art to make and use the invention.

We claim:

1. A low profile medical device having a lengthwise axis, a radially compressed configuration and a radially expanded configuration, said low profile medical device comprising:
    a first wire member having first and second ends and defining a first arcuate path with a first curve disposed between the first and second ends, the first arcuate path comprising only a single sigmoidal curve;
    a second wire member having third and fourth ends and defining a second arcuate path with a second curve disposed between the third and fourth ends, the second arcuate path comprising only a single sigmoidal curve;
    a third wire member having fifth and sixth ends and defining a third arcuate path with a third curve disposed between the fifth and sixth ends;
    a first connector connecting the first, third and fifth ends; and
    a second connector connecting the second, fourth and sixth ends and spaced from the first connector on said lengthwise axis of said medical device;
    wherein substantially no portion of said medical device is disposed on a first transverse axis of said medical device opposite the first, third and fifth ends and substantially no portion of said medical device is disposed on a second transverse axis of said medical device opposite the second, fourth and sixth ends when said medical device is in said radially expanded configuration.

2. The low profile medical device of claim 1, wherein the second connector comprises a separate member attached to the second, fourth and sixth ends.

3. The low profile medical device of claim 1, wherein the first connector comprise a separate member attached to the first, third and fifth ends.

4. The low profile medical device of claim 1, wherein the first curve is disposed substantially opposite the second curve.

5. The low profile medical device of claim 1, wherein the first, second and third wire members are formed of nitinol.

6. The low profile medical device of claim 1, wherein the first, second and third wire members are formed of stainless steel.

7. A low profile medical device having a lengthwise axis, a radially compressed configuration and a radially expanded configuration, said low profile medical device comprising:
    a first wire member having first and second ends and defining a first arcuate path with a first curve disposed between the first and second ends, the first arcuate path comprising only a single sigmoidal curve;
    a second wire member having third and fourth ends and defining a second arcuate path with a second curve disposed between the third and fourth ends, the second arcuate path comprising only a single sigmoidal curve;
    a first connector connecting the first and third ends;
    a second connector connecting the second and fourth ends and spaced from the first connector on said lengthwise axis of said medical device; and
    a third wire member extending from the first connector to the second connector and defining a third arcuate path with a third curve disposed between the third and fourth ends, the third arcuate path comprising only a single sigmoidal curve.

8. The low profile medical device of claim 7, wherein the second connector comprises a separate member attached to the second and fourth ends.

9. The low profile medical device of claim 8, wherein the first connector comprises a separate member attached to the first and third ends.

10. The low profile medical device of claim 7, wherein the first curve is disposed substantially opposite the second curve.

11. The low profile medical device of claim 7, wherein the first, second and third wire members are formed of nitinol.

12. The low profile medical device of claim 7, wherein the first, second and third wire members are formed of stainless steel.

13. A low profile medical device having a lengthwise axis, a radially compressed configuration and a radially expanded configuration, said low profile medical device comprising:
    a first series of at least three wire members, each wire member of the first series of wire members defining first and second ends and an arcuate path comprising only a single sigmoidal curve;
    a second series of at least three wire members, each wire member of the second series of wire members defining first and second ends and an arcuate path comprising only a single sigmoidal curve;
    a first connector connecting the first ends of the wire members of the first and second series of wire members; and
    a second connector connecting the second ends of the wire members of the first and second series of wire members, the second connector spaced from the first connector on said lengthwise axis of said medical device.

14. The low profile medical device of claim 13, wherein the second connector comprises a separate member attached to the second ends of the wire members of the first and second series of wire members.

15. The low profile medical device of claim 14, wherein the first connector comprises a separate member attached to the first ends of the wire members of the first and second series of wire members.

16. The low profile medical device of claim 13, wherein the second connector is integrally formed with the second ends of the wire members of the first and second series of wire members.

17. The low profile medical device of claim 16, wherein the first connector is integrally formed with the first ends of the wire members of the first and second series of wire members.

18. The low profile medical device of claim 13, wherein a sigmoidal curve defined by a wire member of the first series of wire members is disposed substantially opposite the sigmoidal curve defined by a wire member of the second series of wire members.

19. The low profile medical device of claim 13, wherein the wire members of the first and second series of wire members are formed of nitinol.

20. The low profile medical device of claim 13, wherein the wire members of the first and second series of wire members are formed of stainless steel.

* * * * *